(12) United States Patent
Maurer et al.

(10) Patent No.: US 7,798,003 B2
(45) Date of Patent: Sep. 21, 2010

(54) ULTRASOUND PROBE ARRANGEMENT

(75) Inventors: Albrecht Maurer, Seligenstadt (DE);
Michael Strauss, Mömbris (DE);
Walter De Odorico, Kelkheim (DE);
Wolfgang Haase, Sailauf (DE); Roman Koch, Blankenbach (DE)

(73) Assignee: GE Inspection Technologies, GmbH, Hurth (DE)

( * ) Notice: Subject to any disclaimer, the term of this patent is extended or adjusted under 35 U.S.C. 154(b) by 293 days.

(21) Appl. No.: 11/914,619

(22) PCT Filed: May 18, 2006

(86) PCT No.: PCT/EP2006/004697
§ 371 (c)(1),
(2), (4) Date: Dec. 3, 2007

(87) PCT Pub. No.: WO2006/122798
PCT Pub. Date: Nov. 23, 2006

(65) Prior Publication Data
US 2009/0126496 A1    May 21, 2009

(30) Foreign Application Priority Data
May 18, 2005    (DE) ................ 10 2005 022 729

(51) Int. Cl.
*G01N 29/28* (2006.01)
(52) U.S. Cl. .......................... 73/644; 73/632

(58) Field of Classification Search ............... 73/644, 73/628, 632; 310/328, 334–336
See application file for complete search history.

(56) References Cited
U.S. PATENT DOCUMENTS
3,908,445 A    9/1975 Verdon et al.
(Continued)

FOREIGN PATENT DOCUMENTS
DE    2916933 A    10/1980
(Continued)

*Primary Examiner*—J M Saint Surin
(74) *Attorney, Agent, or Firm*—Global Patent Operation; Mark A. Conklin

(57) ABSTRACT

The invention relates to an ultrasound probe arrangement (14, 16) for coupling ultrasonic signals toward a component (12), which is to be inspected, by using the water open jet method, with a probe (24; 124), which is placed inside a jet nozzle (26; 126) and having a multitude of ultrasonic transmitting and/or receiving elements (25; 125) and at least one liquid inlet (28; 128) as well as at least one liquid outlet (30; 130). In order to improve the flow of water inside the jet nozzle, the invention provides that: one or more preliminary or filter chambers (FK1, FK2, FK3) are situated upstream from a flow space (36, 136); each preliminary or filter chamber (FK1, FK2, FK3) comprises a dividing wall (TW1, TW2, TW3) having flow channels (SK1, SK2, SK3) running perpendicular to the direction of flow; the number of flow channels (SK1, SK2, SK3) in each dividing wall (TW1, TW2, TW3) increases in the direction of flow, and; the diameter of the flow channels (SK1, SK2, SK3) in each dividing wall (TW1, TW2, TW3) decreases in the direction of flow.

8 Claims, 4 Drawing Sheets

U.S. PATENT DOCUMENTS

Figure 1:
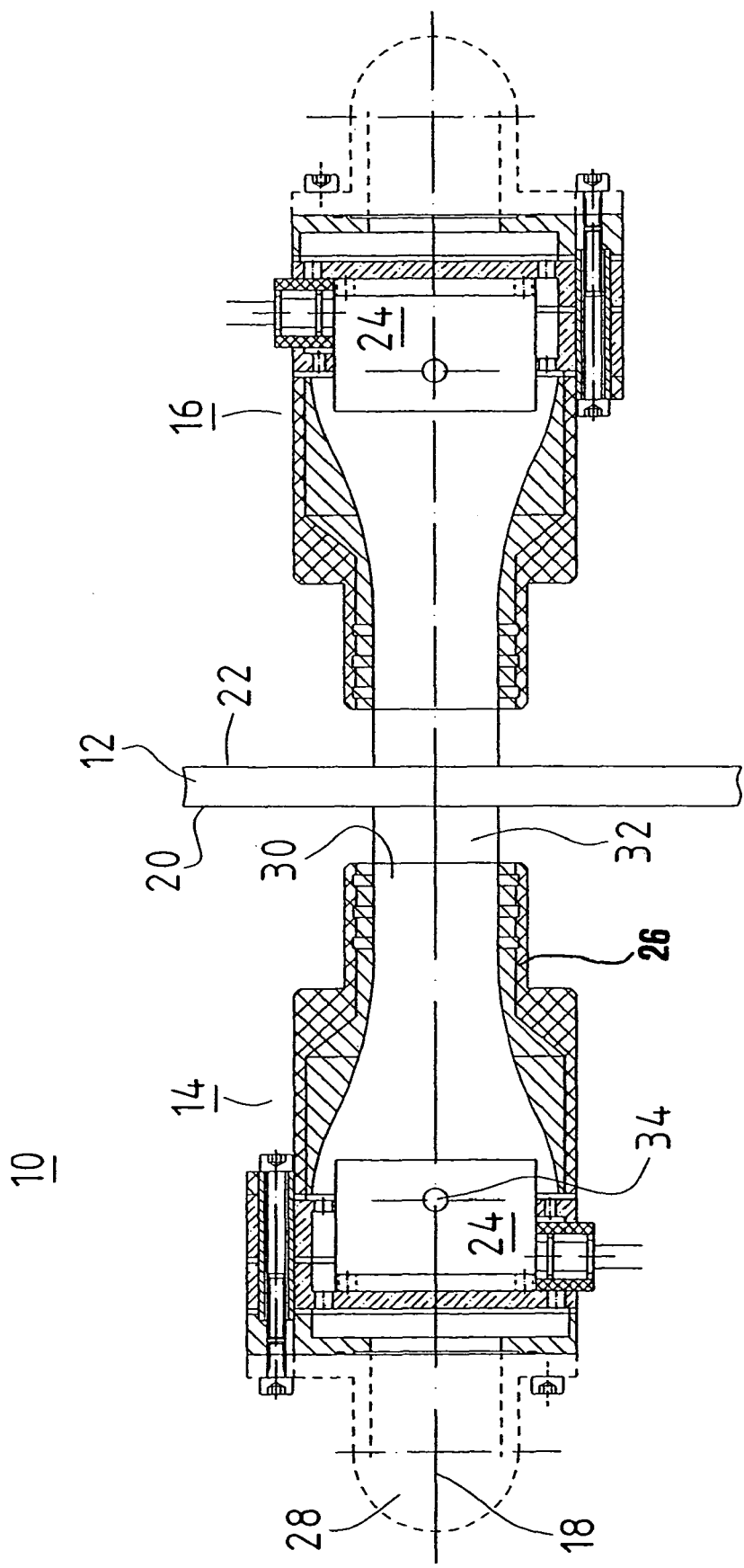

| | | | |
|---|---|---|---|
| 4,507,969 A * | 4/1985 | Djordjevic et al. | 73/644 |
| 4,558,598 A | 12/1985 | Young | |
| 4,726,231 A * | 2/1988 | Tretout et al. | 73/644 |
| 5,001,932 A * | 3/1991 | Light et al. | 73/644 |
| 5,242,119 A | 9/1993 | Jariyasunant | |
| 5,373,743 A * | 12/1994 | Abrahams | 73/644 |
| 5,431,342 A | 7/1995 | Saripalli et al. | |
| 7,404,327 B2 * | 7/2008 | Barco Villalba et al. | 73/644 |
| 7,607,594 B2 * | 10/2009 | Saripalli | 239/590.3 |
| 2002/0104906 A1 | 8/2002 | Freier | |

FOREIGN PATENT DOCUMENTS

| | | |
|---|---|---|
| DE | 195 21 523 A1 | 12/1996 |
| GB | 2194051 A | 2/1988 |

\* cited by examiner

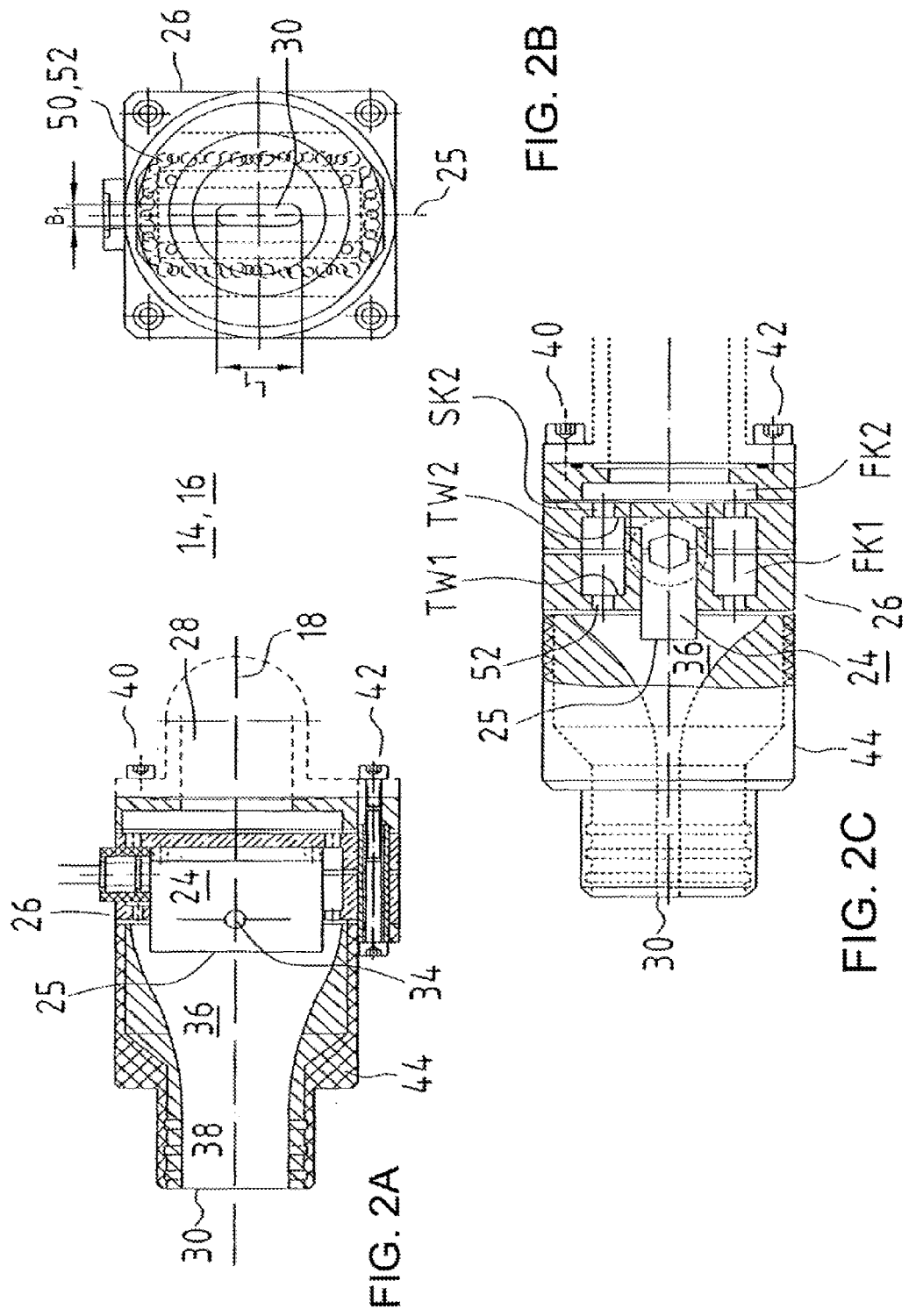

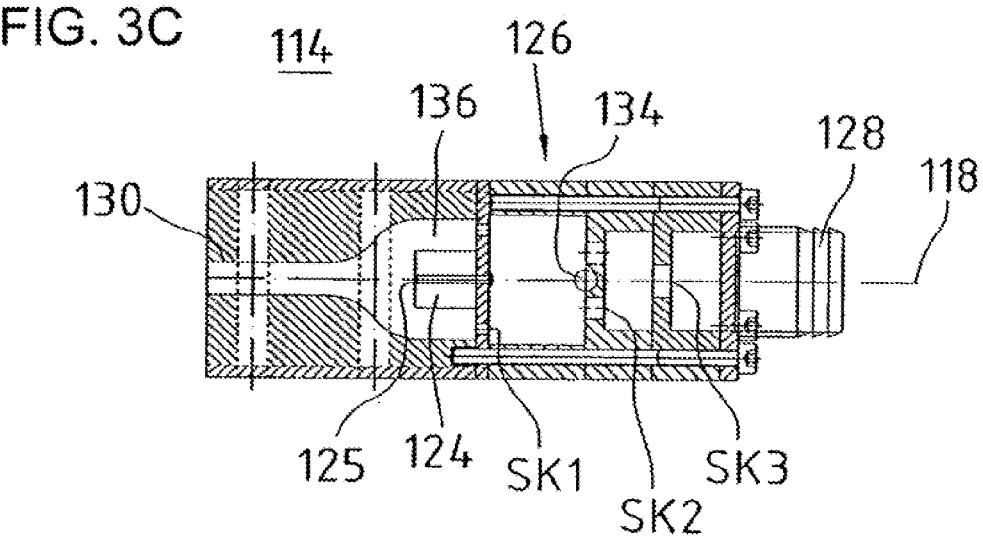

ULTRASOUND PROBE ARRANGEMENT

This application is the US National Phase of International Application PCT/EP2006/004697 filed on May 18, 2006, which claims priority to German Application Serial No. 10 2005 022729.5, both of which are incorporated in their entirety by reference herein.

The invention relates to a probe arrangement for coupling ultrasonic signals to a component to be inspected by the water open jet method using a probe located in a jet nozzle and having a multiplicity of ultrasonic transmitting and/or receiving elements and at least one liquid inlet as well as at least one liquid outlet, where at least two of the transmitting and/or receiving elements are assigned to a single liquid jet and where the at least two ultrasonic signals are capable of being coupled to the component by the single liquid jet.

A probe arrangement of this kind is described for example in EP-A-0,164,168. Provided in this device are liquid inlet apertures, downstream of each of which is situated a collection chamber. In the linear direction downstream of the inlet apertures are located deflecting plates, running horizontally, which extend over the entire length of the chamber. Although horizontal distribution of the water can be obtained with the deflecting plates, these are not suitable for producing a laminar flow.

An ultrasound instrument for the trouble-free inspection of a component by the water open jet technique is likewise described in GB-A-2,194,051. In this arrangement, too, the ultrasonic signals are produced by a probe having a multiplicity of transmitting and/or receiving elements, where at least two of the ultrasonic signals are coupled to the component to be inspected by a single liquid jet.

Described in DE-A-2,916,933 is a method for ultrasound workpiece inspection, where, using the water open jet technique (SQUIRTER technique), an ultrasonic signal is coupled to the component to be inspected. There it is provided that a plurality of laminar hydraulic jets lying close together are used for coupling the ultrasonic signal and that the individual hydraulic jets are controlled by separate ultrasonic transducers with variably adjustable phase relationships (phased arrays).

A so-called array consists of a plurality of individual radiators, which of themselves radiate spherical waves. Each individual radiator is controlled by a separate transmitter. In this way the phase relationships of the individual radiators can be varied. A linear phase relationship results in scanning, a quadratic phase relationship results in jet focusing. The two phase relationships combined convert the array into a radiator with a swiveling acoustic radiation direction and an adjustable focusing zone.

A jet nozzle for performance of the method is characterized in that it is provided on its front surface with a multiplicity of holes, from each of which emerges a free water jet. Each of the jets carries an ultrasonic ray, which is excited by a separate ultrasonic transducer in each instance. The phase relationship between all individual rays is adjustable.

Because of turbulence upon impact of each of the individual water jets, the diameter of which is at least one-half wavelength, e.g., about 1 mm, turbulence may be produced which may result in a weakened acoustic signal and hence in an incorrect evaluation.

Because of the small diameter of the jet in the range of 1 mm and the small distance apart from each other of the free jets, which likewise lies in this order of magnitude, only a small amount of energy can be coupled in, with the consequence that the arrangement has a high signal-to-noise ratio, which likewise may result in measurement inaccuracies.

The present invention is based on the problem of developing a probe arrangement of the kind mentioned at the beginning so that the flow of water within the jet nozzle is improved.

This problem is solved as relates to a method inter alia in that one or more preliminary or filter chambers are situated upstream of a flow space, in that each preliminary or filter chamber comprises a dividing wall having flow channels running perpendicular to the direction of flow, in that the number of flow channels in each dividing wall increases in the direction of flow and in that the diameter of the flow channels in each dividing wall decreases in the direction of flow.

The probe arrangement is characterized in that a laminar water flow within the flow space is obtained in that one or more preliminary or filter chambers are situated upstream of the flow space, where each filter chamber has a dividing wall having flow channels running perpendicular to the direction of flow, where the number of flow channels in each dividing wall increases in the direction of flow and where the diameter of the flow channels in each dividing wall decreases in the direction of flow. The flow channels may be designed as bores.

It is in addition provided that the liquid inlet is located along a central axis of the jet nozzle. In the case of two or more liquid inlets, these are placed parallel or substantially parallel to a plane formed by the liquid jet.

To avoid additional reflection and scattering, the jet nozzle preferably is made of a synthetic material having low acoustic velocity, such as acrylic glass.

Owing to the flat water jet, laminar flow is maintained until impact on the surface of the component to be inspected, so that turbulence is virtually ruled out, as a result of which trouble-free acoustic coupling as well as trouble-free reception of reflected acoustic signals is made possible.

The water jet used is a flat-section jet with a width B in the range of 4 mm $\leq$ B $\leq$ 20 mm and a length L in the range of 10 mm $\leq$ L $\leq$ 120 mm, where the width B and the length L are greater than one-half the wavelength of the acoustic signals used.

Since the acoustic waves within the liquid flat-section jet are not conducted according to the principle of a fiber-optic waveguide, as takes place in individual circular-section jets according to the prior art, the subsonic signals of the width B can be coupled in with high energy, so that all together a high signal-to-noise ratio can be obtained.

Because of the length L, one side of the acoustic radiation angle and/or the focusing zone can be adjusted in a wide range. Higher resolution in comparison to the prior art can also be obtained.

Owing to the slot-like water outlet aperture, a substantially flatter water jet is produced, the cross section of which is shaped rectangular, with the possibility of adjusting the ultrasonic signals in their acoustic radiation direction and their focusing zone by the prescribed range of the flat jet.

Figure 3A:
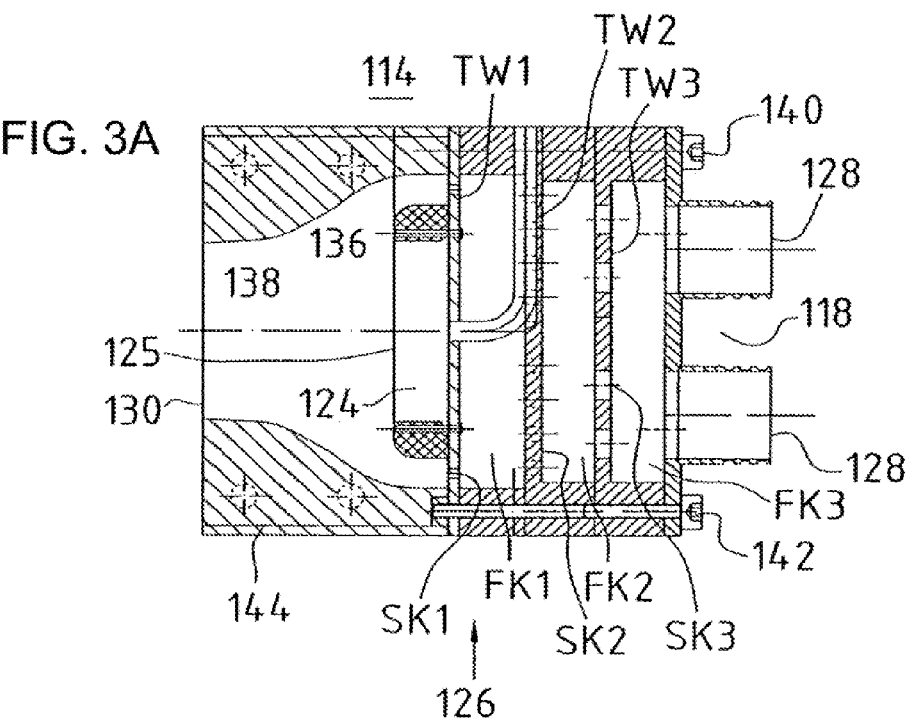
Figure 3B:
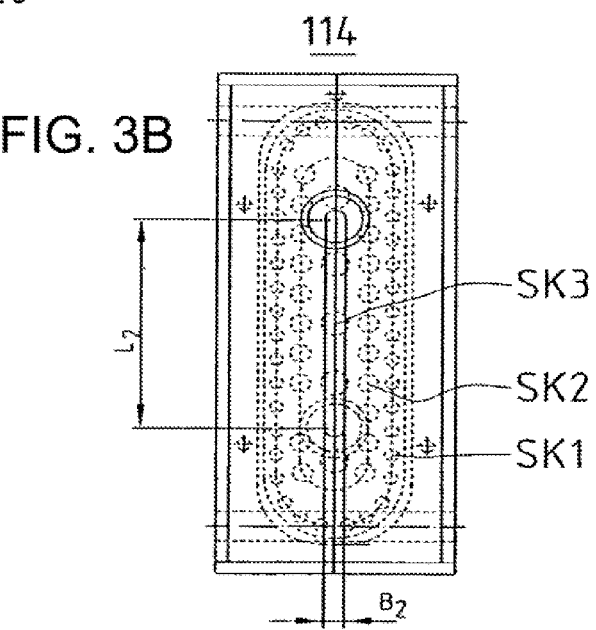

There, the jet nozzle is designed as a flat-section jet nozzle, comprising a substantially funnel-shaped flow space, which is converted into a substantially rectangular outlet channel. The ultrasonic transmitting and/or receiving elements located in the probe preferably are arranged in a plane formed by the liquid jet, the liquid flowing coaxially around the probe. Additional details, advantages and features of the invention are found not only in the claims, the features to be found in the latter—by themselves and/or in combination—, but also in the following preferred exemplary embodiments to be found in the drawing, wherein FIG. 1 shows an arrangement for ultrasonic inspection of a component by the water open jet technique, FIGS. 2a, 2b, 2c show a first embodiment of a probe arrangement and FIGS. 3a, 3b, 3c show a second embodiment of a probe arrangement.

FIG. 1 shows an arrangement for inspecting a component 12 by means of ultrasonic signals, which are coupled to the component 12 to be inspected by using the water open jet technique.

The arrangement 10 comprises a first probe arrangement 14 as well as a second probe arrangement 16, which are arranged facing one another on a common central axis 18 and in each instance expose a surface 20, 22 of the component 12 to ultrasonic waves according to the transmission principle.

The probe arrangements 14, 16 have substantially the same structure, which is explained in detail below with the probe arrangement 14. The probe arrangement 14 comprises a probe 24 with a multiplicity of ultrasonic transmitting and/or receiving elements 25, which are arranged in a row. The transmitting and/or receiving elements are adjustable in their phase relationships by a control unit, whereby the acoustic radiation direction and/or the focusing zone are variable.

The probe 24 is placed inside a jet nozzle 26, which has a liquid inlet 28 and a liquid outlet 30. The liquid outlet is designed in such a way that it produces a laminar flat jet 32 of liquid forming a plane, by which the ultrasonic signals generated in the probe 24 can be coupled to the component 12.

There, the flat liquid jet 22 forms a coupling channel, in which the ultrasonic signals are adjustable in their acoustic radiation direction and/or their focusing zone. The probe arrangement may be tilted about a rotational axis_34 in a plane formed by the liquid jet 32.

Additional details concerning the actual structure of the probe arrangement 14, 16 are described with reference to FIGS. 2 and 3.

FIGS. 2a, 2b and 2c show a variety of views of the probe arrangement 14 of FIG. 1. The jet nozzle 26 is designed as a flat-section jet nozzle and comprises a substantially funnel-shaped flow space 36, which is converted into a substantially rectangular outlet channel 38 that finally terminates in the outlet aperture 30. A cross section of the outlet aperture 30 is shown in FIG. 2b. In the exemplary embodiment shown, the cross section of the outlet aperture 30 corresponds substantially to an elongated hole with the length L in the range of 10 mm$\leq$L$\leq$40 mm, preferably L=20 mm and a width B in the range of 4 mm$\leq$B$\leq$12 mm, preferably B=6 mm.

One or more filter chambers FK1, FK2 are situated upstream of the flow space 36, in order to filter out turbulence from the liquid flowing in through the inlet aperture 28. For setting a constant flow, the liquid is carried through one or more individually adjustable flow regulators. The flow chambers 36 and the filter chambers FK1, FK2 are separated from each other by dividing walls TW1, TW2 running transverse to the direction of flow, while in the dividing walls TW1, TW2 flow channels SK1, SK2 are in each instance arranged in such a way that the liquid flows around the probe 24 substantially coaxially. Lastly, the flow discharges into the flow channel 36 and in the latter is formed into laminar flow. FIG. 2b shows that the flow channels SK1, SK2 are adapted to the outer rectangular contour of the probe 24. The filter chambers FK1, FK2 are connected by connecting elements 40, 42 with a nozzle element 44 accommodating the flow space 36 and the outlet channel.

FIGS. 3a, 3b and 3c show another embodiment of a probe arrangement 114, in which the components corresponding to the first exemplary embodiment are identified by a reference numeral increased by 100.

This embodiment differs from the embodiment of FIG. 2 in that the outlet aperture 130 has a length L in the range of 40 mm$\leq$L$\leq$120 mm, preferably L=90 mm and a width B in the range of 4 mm$\leq$B$\leq$20 mm, preferably B=8 mm, so that all together a wider laminar liquid jet can be produced for coupling of the ultrasonic waves.

The probe 124 is located substantially entirely in the flow chamber 136, the transmitting/receiving elements 125 of the latter being located in a plane formed by the liquid jet 32.

Unlike the first embodiment, the flat-section jet nozzle 126 has a total of three filter chambers FK1, FK2, FK3, which are placed one after another in the direction of flow. The filter chambers FK1, FK2, FK3 are separated from each other by dividing walls TW1, TW2, TW3, each dividing wall TW1, TW2, TW3 having flow channels SK1, SK2, SK3. The number of flow channels SK1, SK2, SK3 in one of the dividing walls TW1, TW2, TW3 increases in the direction of flow, while the diameter of the flow channels SK1, SK2, SK3 of the individual dividing walls decreases in the direction of flow. The filter elements forming the individual filter chambers FK1, FK2, FK3 are connected in series in stacked construction by connecting elements 140, 142 with the nozzle element 140 accommodating the flow channel 138 and the outlet channel 136.

The nozzle element 40, 140 as well as the filter elements FE1, FE2, FE3 may be made of transparent material, such as for example acrylic glass, for inspecting flow behavior.

The invention claimed is:

1. A probe arrangement (14, 16) for coupling ultrasonic signals to a component (12) to be inspected by the water open jet technique, with a probe (24, 124) located in a flow space (36, 136) of a jet nozzle (26, 126), having a multiplicity of ultrasonic transmitting and/or receiving elements (25, 125) and at least one liquid inlet (28, 128) as well as at least one liquid outlet (30, 130), where at least two preliminary or filter chambers (FK1, FK2, FK3) are situated upstream of the flow space (36, 136), where each preliminary or filter chamber (FK1, FK2, FK3) has a downstream dividing wall (TW1, TW2, TW3) having flow channels (SK1, SK2, SK3), said dividing wall (TW1, TW2, TW3) running perpendicular to the direction of flow, where at least two of the transmitting and/or receiving elements (25, 125) are assigned to a single liquid jet (32) and where the at least two ultrasonic signals can be coupled to the component (12) by the single liquid jet (32), characterized in that for the formation of a laminar liquid flow within the flow space (36, 136), the number of flow channels (SK1, SK2, SK3) in the dividing walls (TW1, TW2, TW3) increases in the direction of flow and in that the diameter of the flow channels (SK1, SK2, SK3) in the dividing walls (TW1, TW2, TW3) decreases in the direction of flow, in that the at least two ultrasonic signals already within the flow space (36, 136) can be directly coupled into a single laminar liquid flow and in that the ultrasonic transmitting and/or receiving elements (25, 125) are adjustable in their phase relationships by a control unit for varying an acoustic radiation direction and/or focusing zone (phased array).

2. The probe arrangement according to claim 1, characterized in that the flow channels (SK1, SK2, SK3) are designed as bores.

3. The probe arrangement according to claim 1, characterized in that the liquid inlet (28, 128) is placed along a central axis (18, 118) of the jet nozzle (14, 114).

4. The probe arrangement according to claim 1, characterized in that in the case of two or more liquid inlets (18, 118) these are located parallel or substantially parallel in a plane formed by the liquid jet (32).

5. The probe arrangement according to claim 1, characterized in that the jet nozzle (26, 126) is made of a synthetic material such as acrylic glass.

6. The probe arrangement according to claim 1, characterized in that individual flow regulators are situated upstream of the liquid inlets (18, 118).

7. The probe arrangement according to claim 1, characterized in that the jet nozzle (26, 126) is designed as a flat-section jet nozzle having a substantially funnel-shaped flow space (36, 136) which is converted into a substantially slot-like outlet channel (38, 138).

8. The probe arrangement according to claim 1, characterized in that the ultrasonic transmitting and/or receiving elements (25, 125) located in the probe (24, 124) are arranged in a plane formed by the liquid jet (32), while the probe (24, 124) is located in the flow space (36, 136) and the liquid flows coaxially around it.

* * * * *